(12) United States Patent
Berzins

(10) Patent No.: US 6,527,549 B1
(45) Date of Patent: Mar. 4, 2003

(54) TWO-PART DENTAL IMPRESSION TRAY

(76) Inventor: Guntars Berzins, 9411 Stanton Ave., Erdenheim, PA (US) 19038

( * ) Notice: Subject to any disclaimer, the term of this patent is extended or adjusted under 35 U.S.C. 154(b) by 0 days.

(21) Appl. No.: 09/966,555

(22) Filed: Sep. 28, 2001

(51) Int. Cl.$^7$ .................................................. A61C 9/00
(52) U.S. Cl. ........................................... 433/45; 433/38
(58) Field of Search ............................. 433/45, 37, 38, 433/39, 40, 41, 42, 43, 44, 46, 47

(56) References Cited

U.S. PATENT DOCUMENTS

| | | | | |
|---|---|---|---|---|
| 2,713,202 A | * | 7/1955 | Jones | 433/38 |
| 2,860,414 A | * | 11/1958 | Brant | 433/43 |
| 3,574,259 A | * | 4/1971 | Jones | 433/38 |
| 4,003,132 A | * | 1/1977 | Beck | 433/42 |

* cited by examiner

*Primary Examiner*—John J. Wilson
(74) *Attorney, Agent, or Firm*—Alfred E. Miller

(57) ABSTRACT

A dental impression tray having two identical one half parts in which each part can be used for making a partial dental impression and wherein the two one half parts can be removably combined for a full mouth impression of a patient.

4 Claims, 3 Drawing Sheets

TWO-PART DENTAL IMPRESSION TRAY

The present invention relates to dentistry, and particularly to a two-part dental impression tray for taking a partial or a full impression of a patient's dentition. In use, an impression material is pressed into the tray, and the tray is inserted in the patient's mouth adjacent to the desired dentition part, whereupon the patient bites into the impression material to create an impression of his or her dentition in the material. After the impression material sets, it is used as a mold to form a dental model by pouring plaster, or the like, into the mold which hardens and sets to form said model of the patient's dentition.

BACKGROUND OF THE INVENTION

Dental impression trays for use with settable impression dental materials are known, such as U.S. Pat. No. 3,401,456 to Goldfogel et al.; U.S. Pat. No. 4,689,010 to Wolfe et al and U.S. Pat. No. 5,513,985 to Robertson. The Goldfogel patent shows a three-part tray assembly in which each part has a planar portion as well as a movable member. Thus, this invention relates to a dental tray structure that can be adjusted in order to compensate for one or more teeth, which may be in irregular positions. The tray is also constructed to be used solely for a full month impression. The patent to Robertson is also constructed and used solely for a full mouth impression. The patent to Wolfe is directed to a dental impression tray, which is either for a partial dentition shown in FIGS. 1 and 2 or as a full impression tray shown in FIG. 9, but there is no showing of an assembly in which a dental impression tray can be easily and rapidly changed from one piece that covers only one half of a dental arch by being removably connected to another one half piece of a dental tray to form an assembly for a full mouth impression. It is to be noted that both the Wolfe and Robinson patents are directed to a dental tray construction, which strives for obtaining a more accurate impression of the patient's dentition.

Briefly stated, the present invention covers a dental impression tray having two identical parts in which one part can be utilized for taking an impression of one half of a dental arch, and in which the second part can be affixed to the first part forming an impression tray for forming a full mouth impression of a patient's teeth.

It is a further feature of the present invention to provide a lightweight dental impression tray that can rapidly and easily removably connect the two parts together to create a full mouth dental impression tray. It is another feature of the present invention in which the connecting parts of the dental impression tray functions as a handle for the tray.

DESCRIPTION OF THE DRAWINGS

In order that the invention may be more clearly understood, it will now be disclosed in greater detail with reference to the accompanying drawings, in which.

DESCRIPTION OF THE PREFERRED EMBODIMENT

Figure 1:
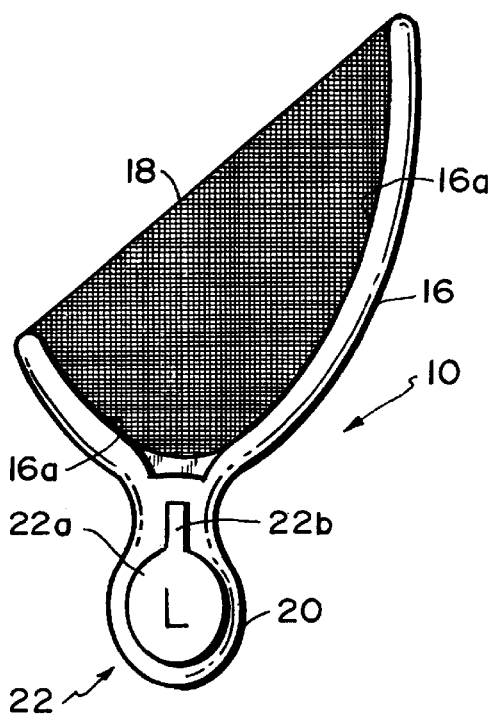
FIG. 1 is a front elevational view of the one half left part of the dental impression tray constructed in accordance wit the teaching of the invention.
Figure 2:
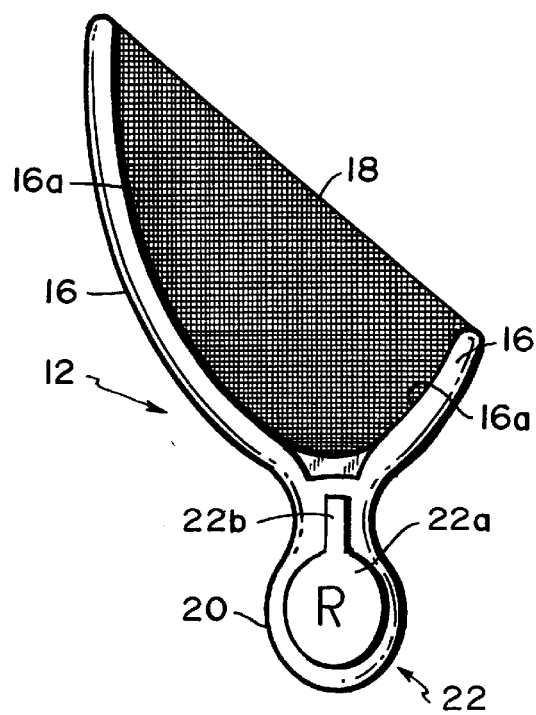
FIG. 2 is a front elevational view of the other one half right part of the dental impression tray constructed in accordance with the teachings of the invention.
Figure 3:
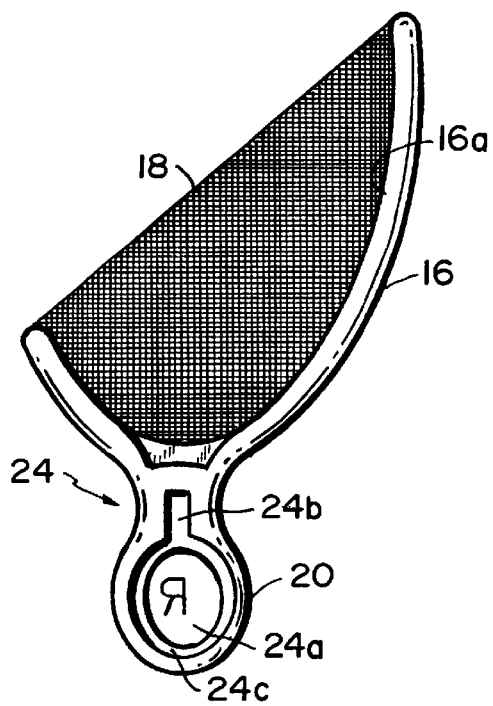
FIG. 3 is a rear elevational view of one half part of the dental impression tray shown in FIG. 2.
Figure 4:
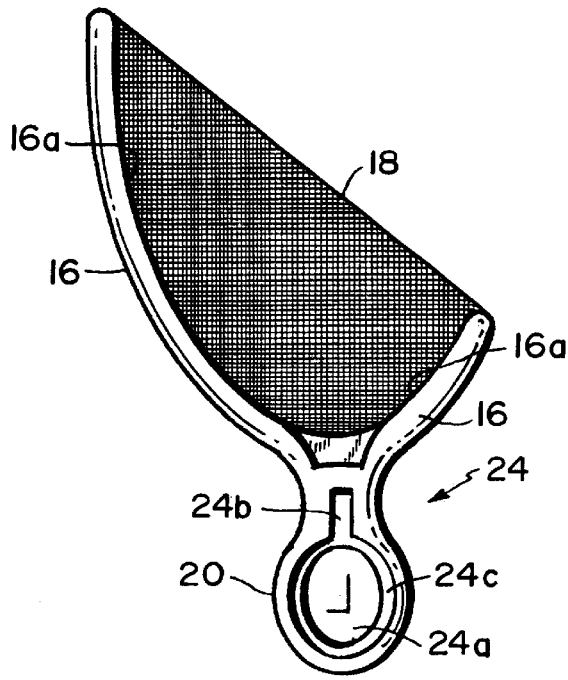
FIG. 4 is a rear elevational view of the one half part of the dental impression tray show in FIG. 1.
Figure 6:
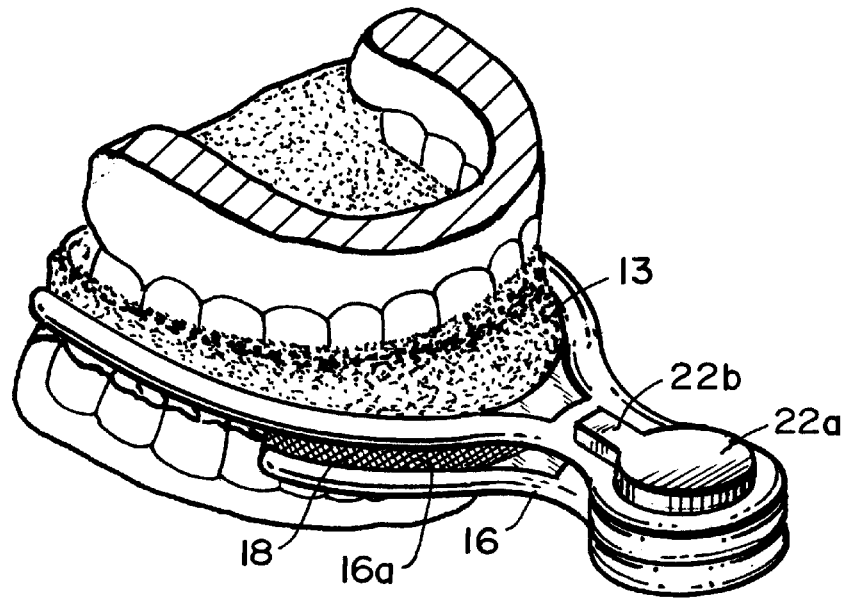
FIG. 6 is a perspective view showing the device shown in FIG. 5 being applied to a patient's dentition.
Figure 5:
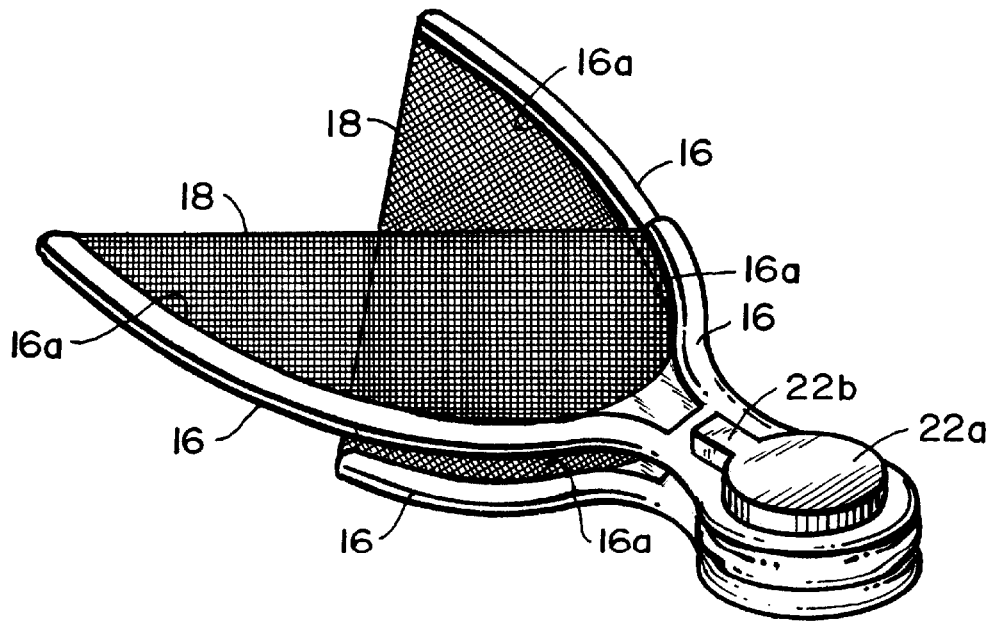
FIG. 5 is a perspective view in which the two one half parts are combined to form a full mouth impression tray.

Referring to the drawings, the dental impression tray of the present invention constitutes left one half part referred to generally by the numeral 10 as shown in FIG. 1, and a right one half part referred to generally by the reference numeral 12 as shown in FIG. 2 of the drawings. The curved dental impression tray frame 16 is fabricated of plastic material, such as a thermoplastic or thermosetting resin, for example polyethylene, or the like. Attached to the inner walls of the frame 16 is a membrane, which takes the form of close mesh, netting gauze or plastic material 18 forming a working surface, which represents one half of a full mouth tray.

If it is desired to have an impression made of one half of a dental arch, either the one half part of the dental tray 10 or 12 is utilized by pouring soft settable dental impression material 13, such as polyvinyl-siloxane on the close mesh 18 working surface. The one half part of the dental tray is used to cover one half of the dental arch if it is only necessary to get an impression of part of the patient's dentition and not the full dentition made of one half of a dental arch, either the one half part of the dental tray 10 or 12 is utilized by pouring soft settable dental impression material, such as polyvinyl-siloxane. The one half part of the dental tray is used to cover half part of the dental tray if it is only necessary to get an impression of part of the patient's dentition, and not the full dentition As seen in FIGS. 1 and 2, the half part of the dental tray can be selected for making a mold of either the right hand or left hand quadrant of the patient's mouth if only a mold is to be made a part of the patient's dentition. However, if a full mouth impression of the patient's teeth is desired the two halves 10 and 12 of the dental impression tray can be attached together.

It should be observed that the two halves of the dental impression tray are identical. Each of the halves has the actuate frame 16 and a mesh material 18 affixed to the inner wall 16a of the frame.

The arcuate frame 16 has a longer part on one side of the tray than the part on the other side of the tray. The mesh material affixed to the frame has the curved marginal edge as well as the linear marginal edge. Depending from the frame 16, which is preferably integral with the frame, is a handle 20, which also functions as a connecting means to the handle of the other half of the dental impression tray, as shown in FIGS. 5–7, 9 and 10. The handle 20 is preferably made of a plastic material of the same type utilized in the fabricating of the frame 12.

The handle 20 on each half 10 or 12 is provided with a banjo-like projection referred to generally by the reference numeral 22 being a circular projection 22a and a linear extension 22b connected to circular projection 22a on one side of the handle, and an identical recess referred to generally by the reference numeral 24 on the opposite side of the handle. The recess 24 is generally circular at 24a, and is provided with a linear recess or groove 24b that is connected to the circular recess 24a, and is provided with a rim 24c.

Figure 7:
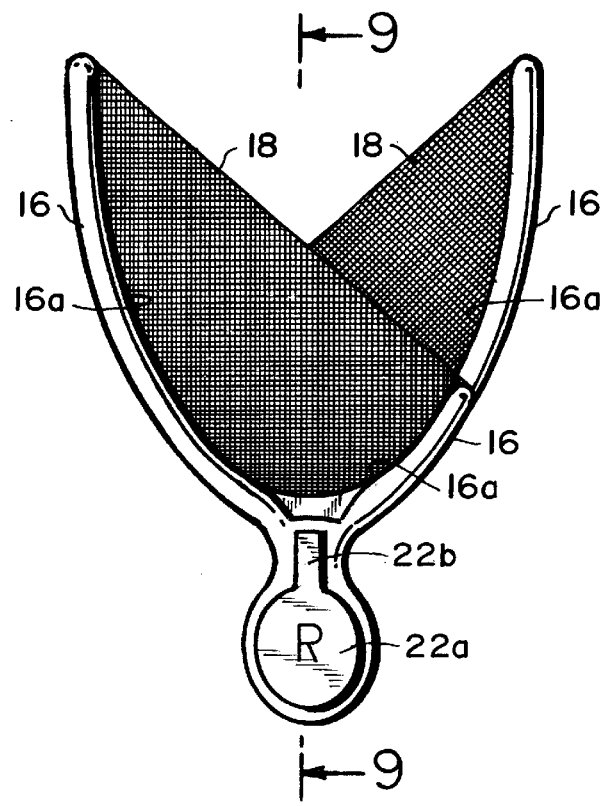
FIG. 7 is a front elevational view of the full mouth dental impression tray.
Figure 8:
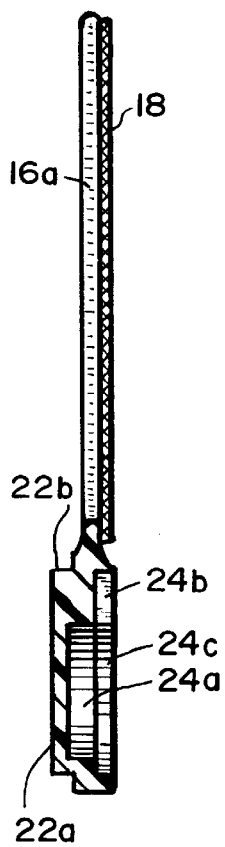
FIG. 8 is a side elevational view of one half of the dental impression tray.
Figure 9:
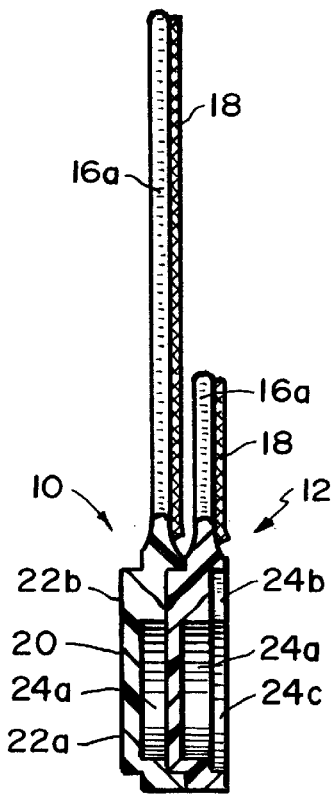
FIG. 9 is a view taken along the lines 9—9 of FIG. 7.
Figure 10:
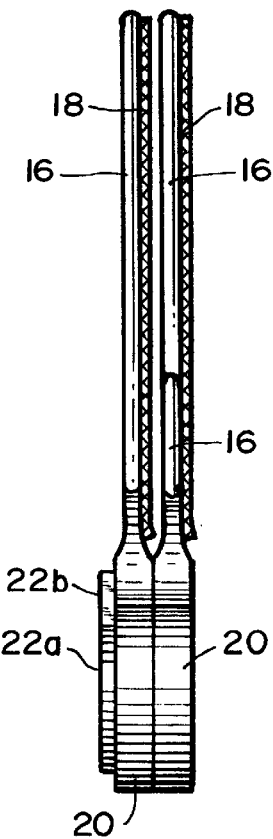
FIG. 10 is a side elevational view of the to halves of the dental impression tray that are removably attached together.

As seen in FIGS. 7, 9 and 10, the two halves 10 and 12 can be removably connected to form a full dental arch impression tray when it is desired to obtain an impression of the patient's full dentition. To accomplish this, the right and left halves are superimposed on each other and removably connected together with right half 12 having its projections 22a and 22b inserted in registry with the corresponding recesses 24a and 24b so that the two halves are securely connected together, but can be separated with a minimum of force. Thus, the handle 20 for the dental impression tray also functions as a means for removably connecting the two halves of the dental impression tray, together, if so desired.

While there has been shown and described an embodiment of the present invention, it will be understood that those may make various changes in form and details of the device illustrated and in its operation skilled in the art without departing from the true spirit of the invention.

What is claimed is:

1. A dental impression tray assembly for part or all of a dentition of a patient comprising a pair of trays in which each tray is anatomically contoured to fit over one half of the dental arch and to be filled with a soft impression material, each of said trays having a handle portion, the handle portion of one tray having an oval projection and an integral rib extending there from, and the handle portion of said other tray having a matching cavity for said oval projection which functionally fits therein, and a matching groove for said rib whereby said trays can be removably attached to form an assembly for making a full mouth impression.

2. A dental impression tray assembly as claimed in claim 1 wherein said oval projection and rib are fabricated of plastic.

3. A dental impression tray assembly as claimed in claim 1 wherein said impression material support member is a membrane having a close mesh with a curved supported marginal edge and an unsupported linear marginal edge.

4. A dental impression tray assembly as claimed in claim 1 wherein the impression material support member is a close-knit mesh membrane.

* * * * *